(12) United States Patent
Tseng

(10) Patent No.: US 6,230,718 B1
(45) Date of Patent: May 15, 2001

(54) TOOTHPICK CONVENIENT FOR CARRYING AND IMPROVED IN PICKING

(76) Inventor: Shao-Chien Tseng, No. 130, Sec. 2, Yang-Shin Rd., Yang-Mei 326, Taoyuan (TW)

( * ) Notice: Subject to any disclaimer, the term of this patent is extended or adjusted under 35 U.S.C. 154(b) by 0 days.

(21) Appl. No.: 09/533,632

(22) Filed: Mar. 22, 2000

(51) Int. Cl.[7] ................................................. A61C 15/00
(52) U.S. Cl. .......................................... 132/321; 132/329
(58) Field of Search ................................. 132/321, 329, 132/323; 433/142, 141, 143; 223/99, 101, 102

(56) References Cited

U.S. PATENT DOCUMENTS

| | | | |
|---|---|---|---|
| 1,382,459 | * | 6/1921 | Bercovici ............................ 132/321 |
| 2,411,118 | * | 11/1946 | Schuster ............................... 223/99 |
| 2,567,408 | * | 9/1951 | Soderberg ............................ 223/99 |
| 3,404,707 | * | 10/1968 | Feld ..................................... 223/99 |
| 3,438,486 | * | 4/1969 | Pinkas ................................. 132/321 |
| 4,090,649 | * | 5/1978 | Cichinski ............................. 223/99 |
| 4,667,860 | * | 5/1987 | Feuerman ............................ 223/99 |
| 4,720,026 | * | 1/1988 | Feuerman ........................... 223/102 |
| 5,230,356 | * | 7/1993 | Villas ................................. 132/329 |
| 5,823,208 | * | 10/1998 | Lin ..................................... 132/329 |
| 6,082,999 | * | 7/2000 | Tcherny et al. ..................... 132/321 |

* cited by examiner

*Primary Examiner*—Ralph A. Lewis
*Assistant Examiner*—Robyn Kieu Doan
(74) *Attorney, Agent, or Firm*—Pro-Techtor International Services

(57) ABSTRACT

The present invention is related to a toothpick convenient for carrying and improved in picking, and is especially directed to a toothpick and a flat receiving sheet for packing. The toothpick is comprised of a picking portion and a shank. Wherein, the picking portion is made of a flexible line; the line is bent to form a tip, two bending portions and an embedded portion. By the flexibility or recoverability from bending provided on the flexible line and by the nature of springs of the two bending portions, the picking portion meets the curvature of the surfaces of teeth and can effectively twisting scrape to clean the walls of teeth easily; the toothpick thereby has the strong effect of clearing off residual food. And a plurality of toothpicks can be provided on the tailing end of the shank of each toothpick with a tearing portion and are arranged and received in a flat receiving sheet to be torn off when a toothpick is needed. Thereby, portability and convenience of use of the toothpicks can be increased.

3 Claims, 8 Drawing Sheets

TOOTHPICK CONVENIENT FOR CARRYING AND IMPROVED IN PICKING

BACKGROUND OF THE INVENTION

1. Field of the Invention

The present invention is related to a toothpick convenient for carrying and improved in picking, and especially to a toothpick of which a picking portion is stretchable and contractible used for picking food residue at a gap between teeth. By the flexibility or recoverability from bending provided on the picking portion of the toothpick, the picking portion meets the curvature of the surfaces of teeth, so that the toothpick can effectively twisting scrape at the gaps between walls of teeth, residual food between teeth can be easily cleared off. The present invention has the industrial effect of lowering cost and capability of mass production by structural simplicity of the shank and the picking portion of the toothpick.

2. Description of the Prior Art

Toothpicks have had their long history of development; any slender rod capable of picking food residue between teeth can be defined as a toothpick. Take a bamboo toothpick customarily and widely used as an example, one end or both ends thereof are tips, they can pierce into the gaps between teeth to pick food residue. However, the tips can only pierce, they don't have the function of twisting scraping, hence efficiency of picking of the tips of the toothpick is limited.

Moreover, in the markets, toothpicks are generally packed in a big package or packed individually for sale. The toothpicks in a big package look too bulky for carrying, and finely packed single toothpick can not afford suitable amount in need, these often make inconvenience and trouble in utilization.

The defects stated above is the motive of study and developing of the present invention, and the inventor of the present invention provides the toothpick of the present invention based on his specific experience of years in contemplation of improvement of toothpicks.

SUMMARY OF THE INVENTION

The main object of the present invention is to provide a toothpick to improve picking capability of the toothpick over a conventional toothpick, and to allow a suitable amount of toothpicks to be parallelly arranged and received in a flat receiving sheet, so that convenience for carrying and using toothpicks can be obtained.

To obtain the aforesaid object of the present invention, in practice, the present invention concerns a toothpick comprised of a picking portion and a shank, and concerns a flat receiving sheet in favor of packing.

Wherein, folding of a plane sheet forms the flat receiving sheet, a plurality of toothpicks can be parallelly arranged and received in the flat receiving sheet. The flat receiving sheet is provided on one end thereof with a foldable cover for the purposed of protecting the toothpicks therein, and thereby forms a toothpick box to allow carrying of a suitable amount of toothpicks for use.

The picking portion of a toothpick is made of flexible metal or nonmetal line (such as stainless steel or Nylon line) with a diameter of 0.2–0.3 mm and is formed by bending as a unit. The picking portion is provided at least with a tip, two bending portions and an embedded portion. The picking portion is provided with flexibility and is recoverable after bending; the bending portions have the nature of springs to be freely stretchable and contractible. The picking portion meets the curvature of the surfaces of teeth by the flexibility and the nature of springs, so that the picking portion can effectively twisting scrape to clean the walls of teeth easily, the toothpick thereby has the strong effect of clearing off residual food.

The shank is made of plastic material, and is wholly in a flat shape in favor of holding by a user in cleaning teeth. The user can thereby more effectively control the angle and direction of the toothpick to get in and retract from the gaps between teeth with twisting and scraping. The tailing end of the shank is provided with a tearing portion to be easily torn off, thereby, when the shank is received in the receiving sheet, a user can conveniently tear it off for using a toothpick.

The present invention will be apparent after reading the detailed description of the preferred embodiment thereof in reference to the accompanying drawings.

DETAILED DESCRIPTION OF THE PREFERRED EMBODIMENT

Figure 1:
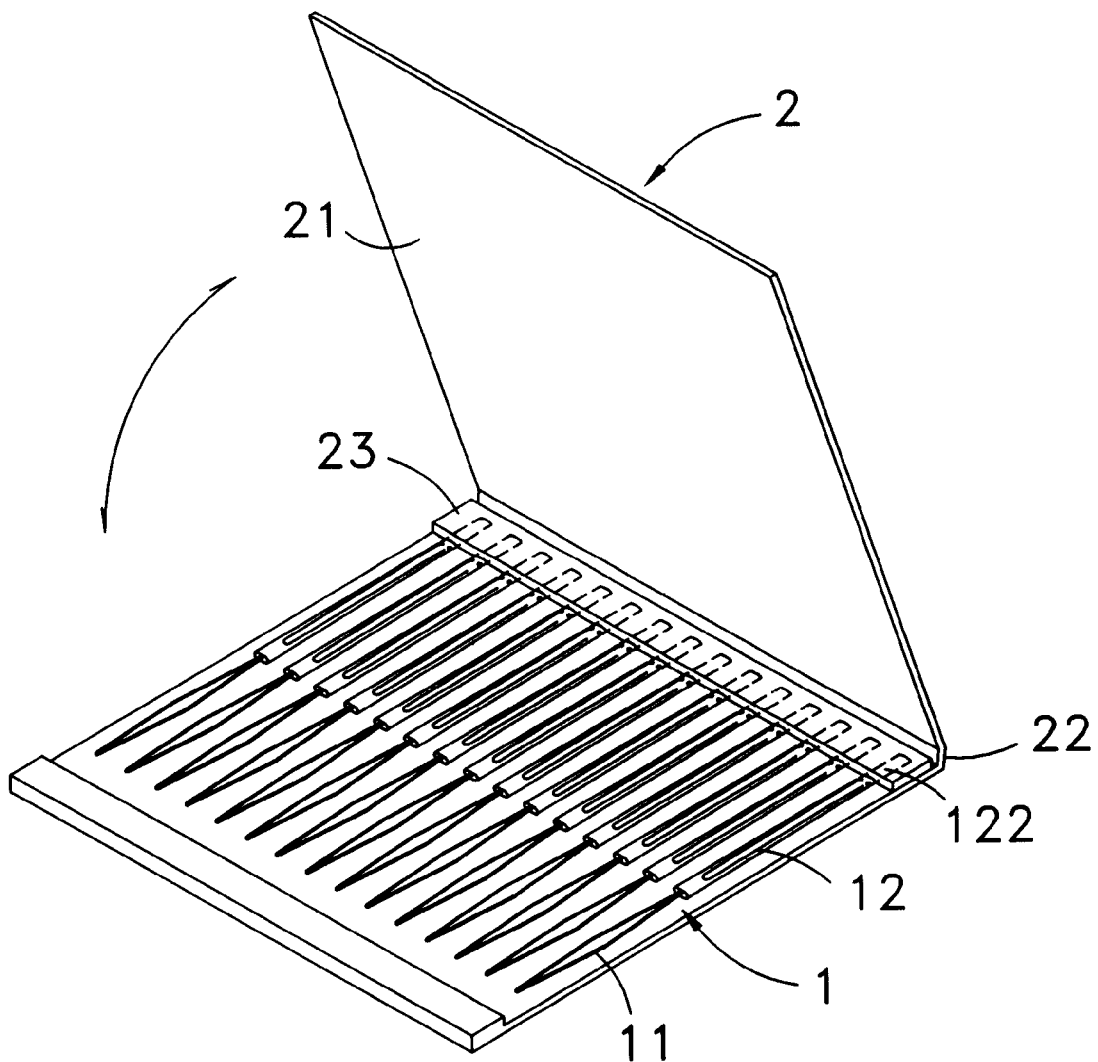
FIG. 1 is a perspective view showing toothpicks of the present invention are received in a flat receiving sheet.

Referring to FIG. 1, the toothpick convenient for carrying and improved in picking of the present invention is directed to a toothpick 1 and a flat receiving sheet 2 for packing. The toothpick 1 is comprised of a picking portion 11 and a shank 12 (referring to FIG. 2).

Wherein, the picking portion 11 is made of flexible metallic or non-metallic material such as stainless steel, PET or Nylon line with a diameter of 0.2–0.3 mm and is formed by bending as a unit; the line is bent to form a bending portion 111 (as shown in FIGS. 2 to 8). The picking portion 11 is in the shape of a rhombus having a tip 111 and an embedded portion 114, the lateral sides of the tip 111 are bent to form two bending portions 112, 113 with a clearance 115 therebetween and provided with a nature of spring to be stretchable and contractible. By the flexibility or recoverability from bending provided on the flexible line, the picking portion 11 can meet the curvature of the surfaces of teeth. So that the picking portion 11 can effectively twisting scrape to clean the walls of teeth easily, the toothpick 1 thereby has the strong effect of clearing off residual food.

Figure 2:
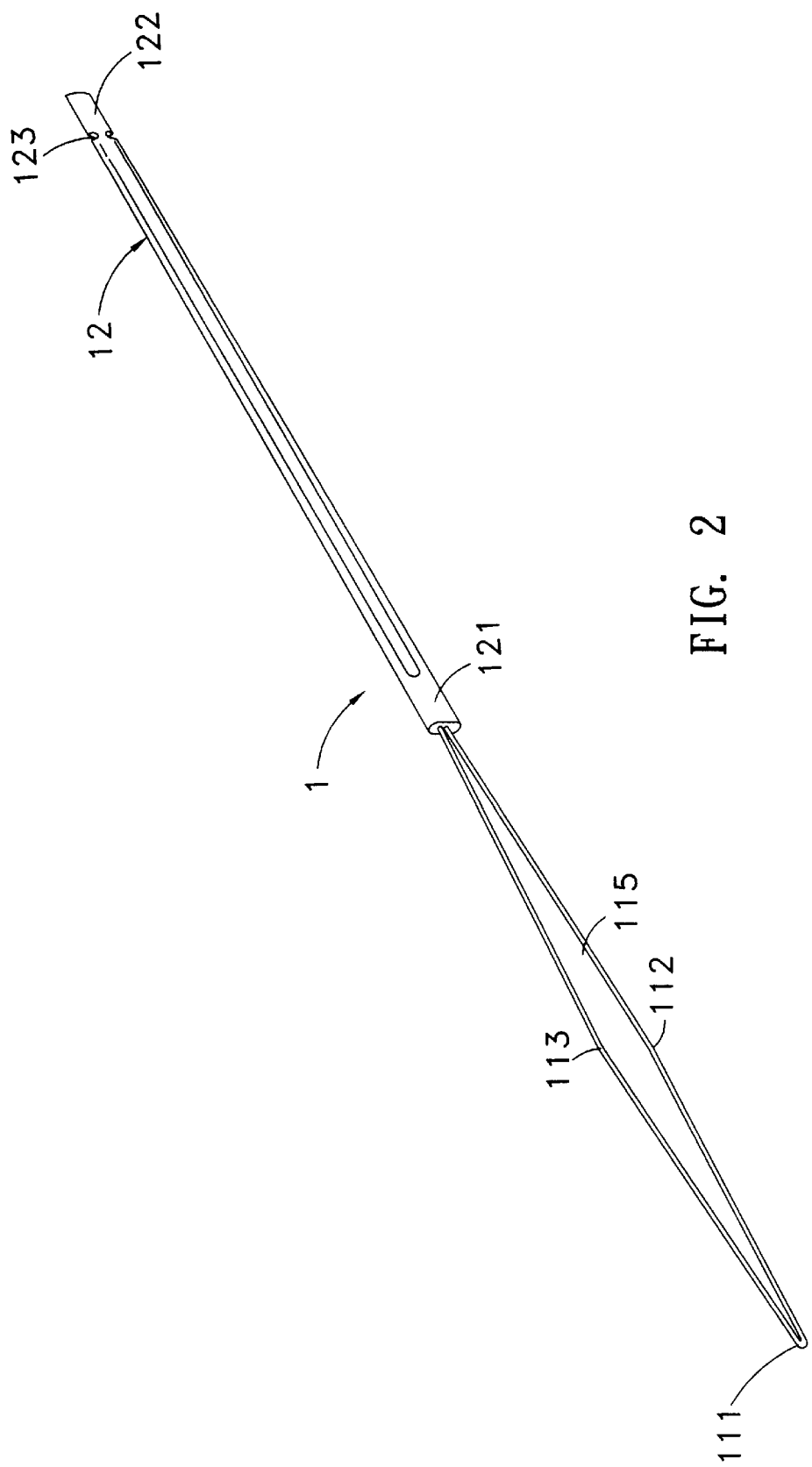
FIG. 2 is a perspective view of a toothpick of the present invention.
Figure 3:
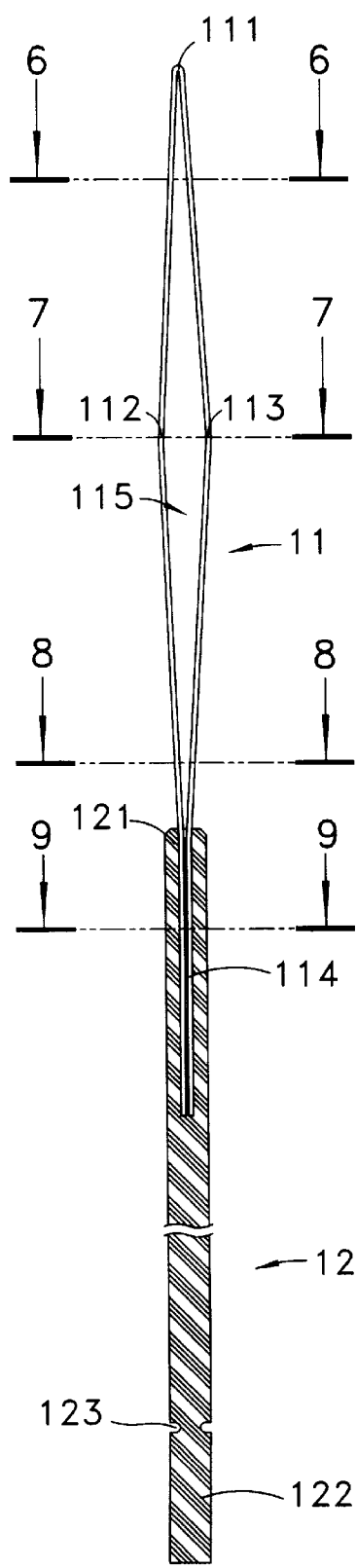
FIG. 3 is a sectional view of the toothpick of the present invention.
Figures 4, 4A, 4B:
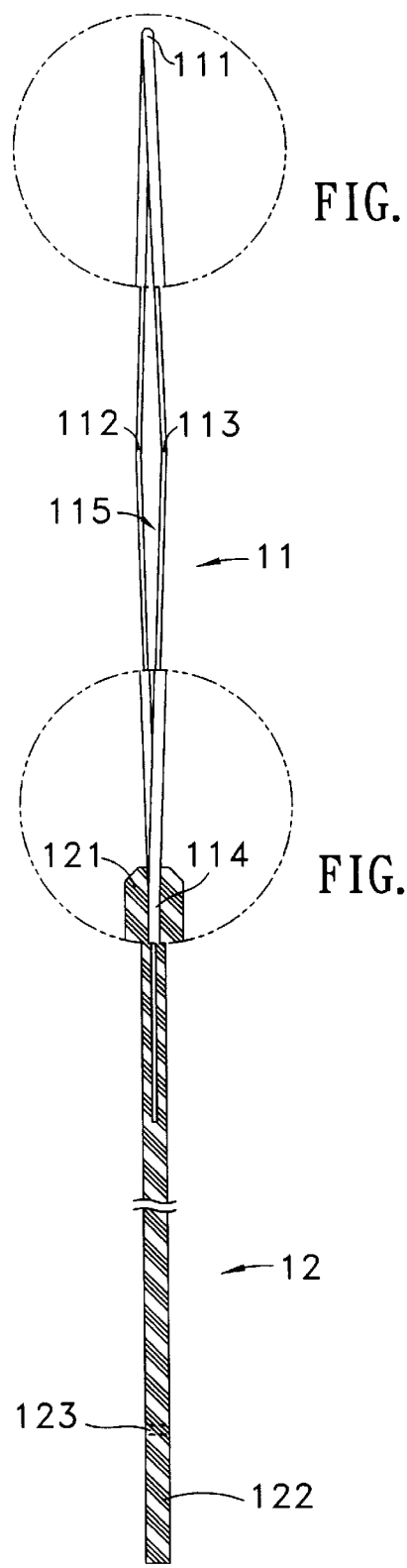
FIG. 4 is a sectional side view of the present invention.
Figure 5:
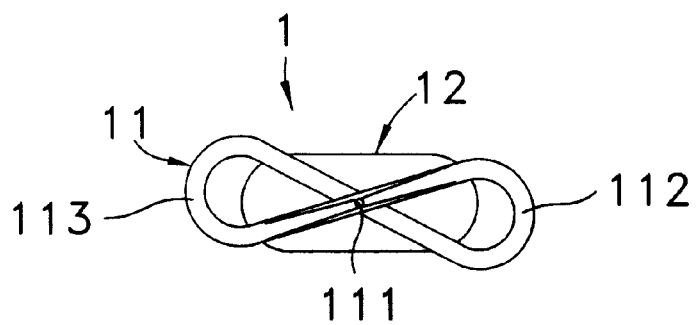
FIG. 5 is a top view of the present invention.
Figure 6:
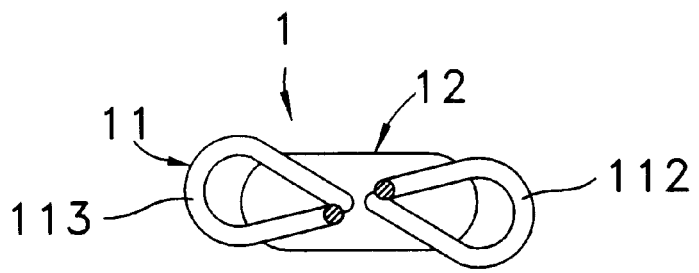
FIG. 6 is a sectional view taken from the section line A—A of FIG. 1 of the present invention.
Figure 7:
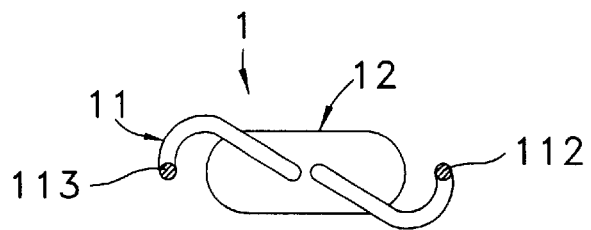
FIG. 7 is a sectional view taken from the section line B—B of FIG. 1 of the present invention.
Figure 8:
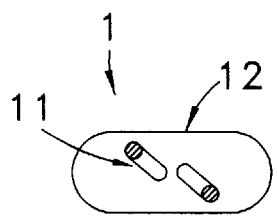
FIG. 8 is a sectional view taken from the section line C—C of FIG. 1 of the present invention.
Figure 9:
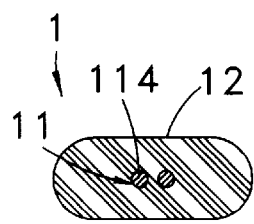
FIG. 9 is a sectional view taken from the section line D—D of FIG. 1 of the present invention.

The shank 12 is made mainly of plastic material such as PET or Nylon (referring to FIG. 2). The upper portion 121 of the shank 12 envelops the embedding portions 114 of the picking portion 11 (referring to FIG. 3). The tailing end 122 of the shank 12 is provided with a tearing portion 123 to be easily torn off. The shank 12 enveloping the picking portion 11 is clamped and contracted to render it to form a flat shape (referring to FIGS. 2, 4 and 9) and to make firm combining of the picking portion 11 with the shank 12. Thereby, a user can conveniently hold it when in deaning teeth.

The flat receiving sheet 2 is formed of a folded plane sheet (referring to FIG. 1). A plurality of toothpicks 1 are parallelly arranged and received on the end portion 22 of the flat receiving sheet 2, and the end portion 22 is covered by and connected with a pressing piece 23 to combine the toothpicks 1 with the flat receiving sheet 2. One end of the flat receiving sheet 2 is provided with a foldable cover 21 for the purpose of covering and protecting the toothpicks 1 therein when the latter are not in need, thereby, a toothpick box with suitable amount of toothpicks 1 therein can be carried for convenient use.

Figure 10:
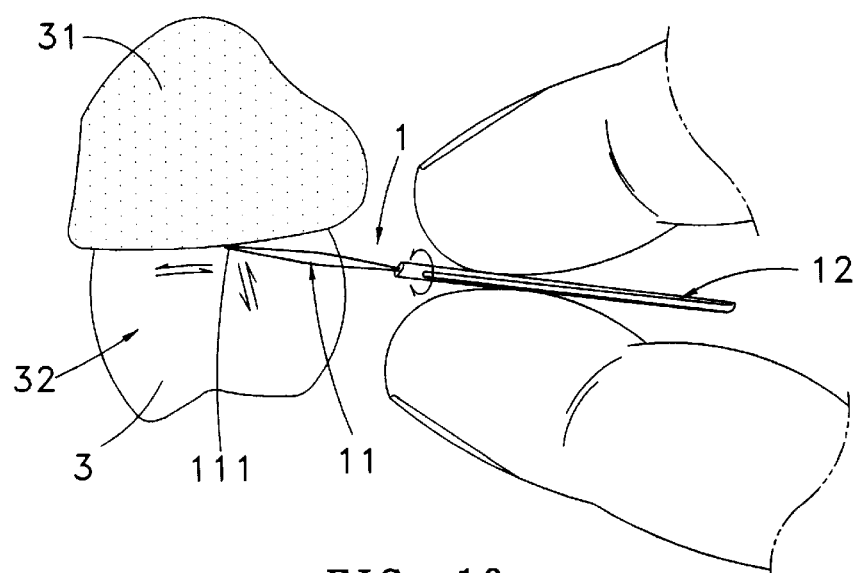
FIG. 10 is a schematic view showing use of the toothpick of the present invention.
Figure 11:
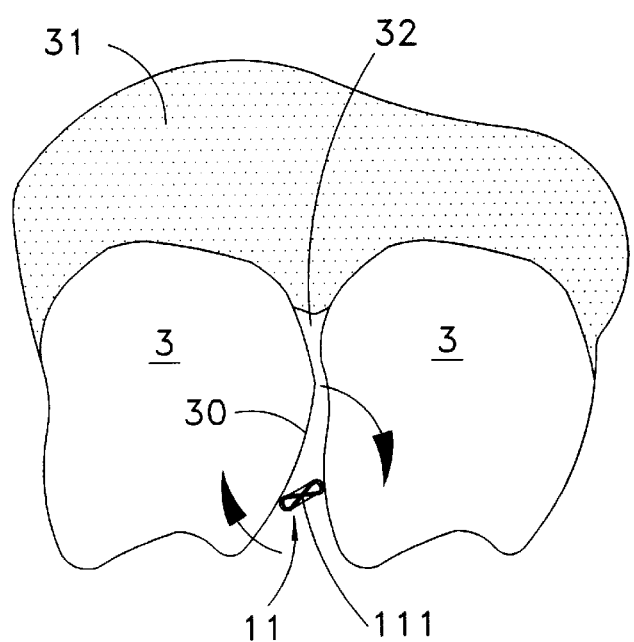
FIG. 11 is another schematic view showing use of the toothpick of the present invention.

In this way, the toothpicks 1 can be carried conveniently. When in use, it only needs to tear off a toothpick 1 at its tearing portion 123 for use, the toothpick 1 can then be inserted with the tip 111 of the picking portion 11 thereof into a gap 32 between two teeth of a row of teeth 3 to pick finer food residue at a tooth wall 30, a gingiva 31 and in the gap 32 with up and down scraping action (as shown in FIG. 10). Meantime, the picking portion 11 is made to be in the shape as a propeller in its cross-sectional view, a user can insert the picking portion 11 into a gap 32 between two teeth of the row of teeth 3 to make an action of twisting to and fro and leftwards and rightwards (as shown in FIG. 11). The slender flexible and elastic thread can clear off finer food residue and more effectively clean the surface of the tooth wall 30, thereby, can more effectively lower the rate of rotting of food residue in a mouth, this can prevent pathological changes of teeth.

It is worthy of mentioning that the bending portions 112, 113 of the picking portion 11 of a toothpick 1 have a dearance 115 therebetween (referring to FIG. 2). The clearance 115 has a function of temporarily holding therein food residue when in clearing the food residue in a gap 32, thereby, the food residue cleared by the picking portion 11 is removed by holding of the clearance 115. The clearance 115 can also easily pry the food residue out of the gap 32, and effectively avoid the food residue to be push into and jammed in the deep of the gap 32. The toothpick 1 thereby has a new function of dirt removing, and is provided with an additional value.

And more, the shank 12 of the toothpick 1 is flat (referring to FIG. 2), the user can conveniently grasp it to dean the row of teeth 3 and more effectively control the angular orientation and picking direction of the toothpick 1. Hence the user can get in and out for twisting scraping the gap 32 and the tooth walls 30 of the row of teeth 3 to further enhance the ability of picking of the toothpick 1. Meantime, the toothpick 1 is comprised only of a picking portion 11 and a shank 12 (referring to FIG. 2), it is structurally simple, and thus can be easily mass produced in a fast speed, and can largely reduce cost of production; it has thereby good industrial utility.

Figure 12:
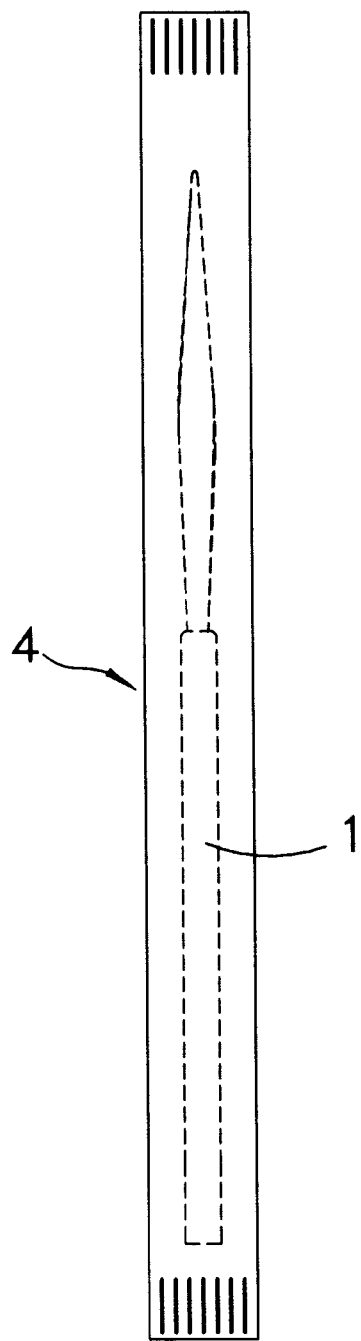
FIG. 12 is schematic view showing another embodiment of the toothpick of the present invention.

The toothpick 1 convenient for carrying and improved in picking of the present invention is adapted to being received in a wrapper 4 closed on both ends (referring to FIG. 12), the wrapper 4 can be made from thin material such as paper or plastic. Therefore, the wrapper 4 is added with commercial additional value, it ensures sanitary quality of a single toothpick 1 in use. Such toothpicks 1 suit banquets, outside orders, quick lunches or fast food as to the scope of application of the present invention.

In conclusion, a toothpick convenient for carrying and improved in picking of the present invention can have the picking portion 11 thereof, by the flexibility or recoverability from bending provided on the flexible line, met the curvature of the surfaces of teeth; and the picking portion 11 can effectively twisting scrape to clean the walls of teeth easily; the toothpick 1 thereby has the strong effect of clearing off residual food. And a plurality of toothpicks 1 can be arranged and received in a flat receiving sheet 2 to form a toothpick box to allow a suitable amount of toothpicks to be conveniently carried for use. Thereby, portability and convenience of use of the toothpicks can be increased. And the toothpick 1 is structurally simple, it can have the valuable industrial utility in ability of easy mass producing in a fast speed and largely reducing cost of production.

Having thus described my invention, what I claim as new and desire to be secured by Letters Patent of the United States are:

1. A toothpick comprising:

a picking portion and a shank, said picking portion is formed from a flexible linear element, free ends of said picking portion are anchored in said shank; wherein two sides of said picking portion are angled outward so as to define an open space between said two sides, said open space being in the shape of a rounded, elongated parallelogram, and said picking portion contracts when a contracting force is applied to a distal end, and said picking portion has sufficient elasticity to return to an original position when said contracting force is removed.

2. The toothpick as defined in claim 1 wherein:

said flexible elongated element is metallic.

3. The toothpick as defined in claim 1 wherein:

said flexible elongated element is non-metallic.

* * * * *